United States Patent

Juge et al.

Patent Number: 5,264,602
Date of Patent: Nov. 23, 1993

[54] CHIRAL PHOSPHINITE-BORANES, THEIR PREPARATION AND USES

[75] Inventors: Sylvain Juge, Orsay; Jean-Pierre Genet, Fontenay-aux-roses; Jean-Alex Laffitte, Pau; Massoud Stephan, Paris, all of France

[73] Assignee: Societe Nationale Elf Aquitaine, Courbevoie, France

[21] Appl. No.: 817,802

[22] Filed: Jan. 9, 1992

[30] Foreign Application Priority Data

Feb. 13, 1991 [FR] France ................. 91 01674

[51] Int. Cl.$^5$ .............. C07F 5/02; C07F 7/08
[52] U.S. Cl. ...................... 556/402; 569/8; 568/2
[58] Field of Search ........... 556/402; 568/2; 564/8

[56] References Cited

U.S. PATENT DOCUMENTS

2,915,543  12/1959  Groszos ................. 556/402
3,131,204  4/1964   Sisler et al. ............ 556/402 X

FOREIGN PATENT DOCUMENTS

9100286  1/1991  World Int. Prop. O.

OTHER PUBLICATIONS

S. Juge et al., Tetrahedron Letters 31 (No. 44), pp. 6357-6360, (1990).

Primary Examiner—Paul F. Shaver
Attorney, Agent, or Firm—Wegner, Cantor, Mueller & Player

[57] ABSTRACT

This invention is concerned with new chiral diphosphinite-borane compound of the formula

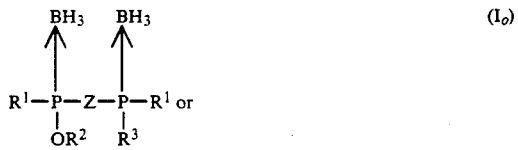
(I$_o$)

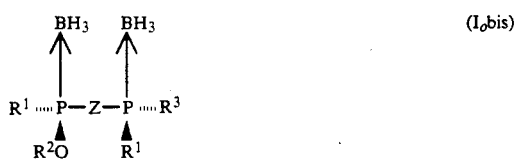

(I$_o$bis)

wherein
$R^1$ and $R^2$, identical or different, represent each a $C_1$-$C_{18}$ alkyl, $C_5$-$C_{18}$ cycloalkyl, $C_7$-$C_{18}$ aralkyl or $C_6$-$C_{14}$ aryl group which can bear functional groups,
$R^3$ represents a $C_1$-$C_{18}$ alkyl, $C_5$-$C_{18}$ cycloalkyl, $C_7$-$C_{18}$ aralkyl, $C_6$-$C_{14}$ aryl, $C_1$-$C_{18}$ alkoxy, $C_5$-$C_{18}$ cycloalkyloxy, $C_7$-$C_{18}$ aralkyloxy or $C_6$-$C_{14}$ aryloxy group,
Z represents a bridge linking the two phosphinite P atoms, said bridge being (i) a hydrocarbon chain having from 1 to 12 catenary C atoms or (ii) a heterohydrocarbon chain comprising from 1 to 12 catenary C atoms and at least one catenary heteroatom selected from the group consisting of O, S, Si, P and N.

These chiral compounds are useful in the manufacture of chiral diphosphine compounds.

9 Claims, No Drawings

CHIRAL PHOSPHINITE-BORANES, THEIR PREPARATION AND USES

FIELD OF THE INVENTION

This invention is concerned with a new class of phosphinite compounds, in particular chiral phosphinite compounds. To be precise, this invention relates to diphosphinite-diphosphinite-borane compounds of the formula $I_0$ hereinafter in which each phosphinite P atom is linked to (or complexed with) a $BH_3$ borane group. These diphosphinite-borane compounds comprise one or several labile or substitutable group allowing a nucleophilic substitution, for instance, by an alkylating, cycloalkylating or arylating group.

This invention is also concerned with methods for preparing said diphosphinite-borane compounds, and with uses of said diphosphinite-borane compounds in the manufacture of diphosphine compounds.

PRIOR ART

It is known that phosphinite compounds, and more particularly the optically active ones, are industrially useful per se as starting materials in the manufacture of other useful chiral products such as for instance phosphine oxides, phosphines, etc.

Several natural and synthetic products can be now manufacture by an asymmetric synthesis route which is catalyzed by means of transition metals, and in particular with catalysts containing optically active organophosphorus ligands. Such an asymmetric synthesis route is performed in order to obtain substances, which are of interest in the field of agriculture, alimentation, pharmacy or perfumery. Known illustrative examples of said asymmetric synthesis route are those concerning the manufacture of L-Dopa, L-phenylalamine, menthol and citronellol.

The preparation of two compounds of the formula

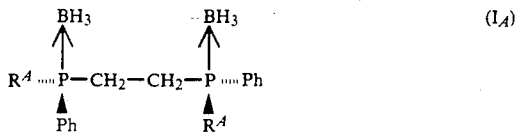

wherein $R^A$ is ortho-anisyl or 2-naphthyl, is known from an article of the co-inventors of this invention, namely S. JUGE et al., Tetrahedron Letters 31, (No. 44), pages 6357–6360 (1990). The two compounds of the formula $I_A$, according to Scheme 2 of said article (see page 6358), are obtained from

(wherein $R^A$ is defined as indicated hereinabove, and $R^B$ is $CH_3$) by reaction of two mols of $I_B$ with (i) s-BuLi, then (ii) $CuCl_2$.

Said article, which is enclosed herewith as reference, also discloses
(a) the obtention of the starting compounds of the formula $I_B$, and
(b) the obtention of chiral 1,2-diphosphinoethane complexes of the formula

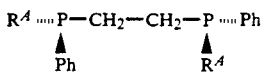

AIM OF THE INVENTION

One goal of this invention is provide new diphosphinite-borane compounds which are different from the prior compounds of the formula $I_A$, either by the structure of the bridge linking the two phosphinite P atoms, or the presence of an oxy-containing group (i.e. $OR^2$) on one of said phosphinite P atoms.

A second goal of this invention is to provide a general method for the preparation of said new diphosphinite-borane compounds of the formula $I_0$, and specific methods for the manufacture of some of these compounds.

SUBJECT OF THE INVENTION

According to a first aspect of this invention is provided a new borane-complexed phosphinite compound which is selected from the group consisting of diphosphinite-borane compounds of the formula

wherein
$R^1$ and $R^2$, identical or different, represent each a $C_1$–$C_{18}$ alkyl, $C_5$–$C_{18}$ cycloalkyl, $C_7$–$C_{18}$ aralkyl or $C_6$–$C_{14}$ aryl group which can bear functional groups,
$R^3$ represents a $C_1$–$C_{18}$ alkyl, $C_5$–$C_{18}$ cycloalkyl, $C_7$–$C_{18}$ aralkyl, $C_6$–$C_{14}$ aryl, $C_1$–$C_{18}$ alkoxy, $C_5$–$C_{18}$ cycloalkyloxy, $C_7$–$C_{18}$ aralkyloxy or $C_6$–$C_{14}$ aryloxy group,
Z represents a bridge linking the two phosphinite P atoms, said bridge being (i) a hydrocarbon chain having from 1 to 12 catenary C atoms or (ii) a heterohydrocarbon chain comprising from 1 to 12 catenary C atoms and at least one catenary heteroatom selected from the group consisting of O, S, Si, P and N.

According to a second aspect of this invention is provided a general method for the preparation of the diphosphinite-borane compounds of the formula $I_0$, said method comprising reacting an organometallic compound deriving from a phosphinite-borane compound with a non-metallic phosphinite-borane compound. Preferably said organometallic compound is an organolithium one.

According to the third aspect of this invention is provided a use of said diphosphinite-borane compounds into other useful disphosphorus derivatives.

To be precise, the diphosphinite-borane compounds according to this invention are, in particular, transformed into diphosphine-borane compounds which either have a high diastereoisomeric purity or are substantially diastereoisomerically pure. Then, these diphosphine-borane compounds are easily decomplexed (decomplexion means here removal of the two $BH_3$ groups) at 50° C. with a secondary amine such as diethylamine.

ABBREVIATIONS

The following abbreviations have been used in the present disclosure for the sake of convenience:

BNPE = bis(naphthylphenylphosphino)ethane, in particular the (−)-BNPE diastereoisomer of the formula:

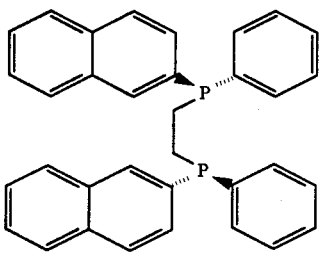

BNPPMDS = bis (naphthylphenylphosphino-methano)-diphenylsilane, in particular the diastereoisomer of the formula:

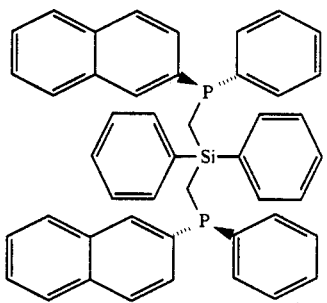

Bu = n-butyl
Bz = benzyl
DIPAMP = 1,2-bis(phenylorthoanisylphosphino)ethane, in particular the (−)-DIPAMP diastereoisomer of the formula:

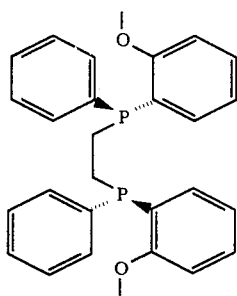

which is also called (R,R)-1,2-bis(phenylorthoanisylphosphino)ethane
Et = ethyl
i-Pr = isopropyl
Me = methyl
MeO = methoxy
MP = melting point
NMR = nuclear magnetic resonance
oAn = orthoanisyl
Ph = phenyl
Pr = n-propyl
s-Bu = sec.-butyl
t-Bu = tert.-butyl
THF = tetrahydrofurane

DETAILED DISCLOSURE OF THE INVENTION

Amongst the functional groups, which are included within the definition of $R^1$ and $R^2$ and which are suitable according to this invention, can be mentioned the $C_1$-$C_4$ alkoxy, CN, $CF_3$, F, Cl, Br and I groups. Thus, $R^1$ and $R^2$ can contain one or several substituted groups selected from the group consisting of $C_1$-$C_4$ alkoxy, CN, $CF_3$, F, Cl, Br, I and mixtures thereof. Preferably, those "functional" groups will be substituted on the aryl moiety of the aryl and aralkyl groups of $R^1$ and $R^2$.

The hydrocarbon moiety of the bridge Z is either an unsaturated hydrocarbon chain or a saturated hydrocarbon chain.

Preferably said bridge Z will have one of the following structures:
(a) —(CH$_2$)$_n$—, and
(b) —(CH$_2$)$_m$—A—(CH$_2$)$_p$—
wherein
n, m and p, identical or different, represent each an integer of from 1 to 6,
A represents O, S, PR, SiR$_2$ or NR, in which R is $C_2$-$C_4$ alkyl, $C_5$-$C_6$ cycloalkyl, $C_6$-$C_{10}$ aryl, benzyl or phenethyl.

More preferably, said bridge Z will represent according to this invention
(a1) —CH$_2$—,
(a2) —CH$_2$CH$_2$—,
(b1) —CH$_2$—O—CH$_2$—,
(b2) —CH$_2$—S—CH$_2$—,
(b3) —CH$_2$—P(Ph)—CH$_2$—,
(b4) —CH$_2$—Si(Me)$_2$—CH$_2$—,
(b5) —CH$_2$—Si(Ph)$_2$—CH$_2$— or
(b6) —CH$_2$—Si(BZ)$_2$—CH$_2$—

When $R^3$ is alkoxy, it contains preferably from 1 to 6 carbon atoms.

The general method for the preparation of a diphosphinite-borane compound of the formula $I_o$ comprises reacting a $BH_3$-containing phosphinite material (i.e. a phosphorus-containing organometallic derivative of a phosphinite compound) of the formula

wherein $R^1$ and $R^2$ are defined as indicated above, and $Z^1$ is Z or a first fragment of said bridge Z,
with a $BH_3$-containing phosphinite compound of the formula

wherein $R^2$ and $R^3$ are defined as indicated above, and $Z^2$ is $R^2$ or the second remaining fragment of bridge Z, $Z^1$ and $Z^2$ being such that $Z^1$−$Z^2$ = Z.

From a chiral point of view (i) a compound according to the formula $I_o$ can be represented by the following structure

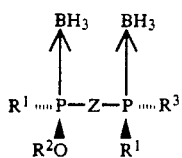  ($I_o$bis)

and (ii) the reaction of $II_A$ with $III_A$ can be illustrated by the following reaction mechanism:

Scheme 1

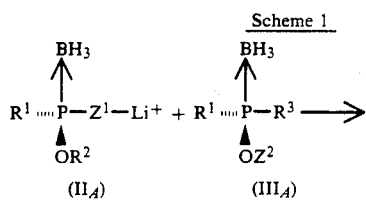

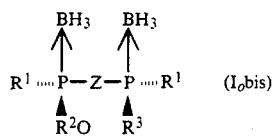 ($I_o$bis)

To be precise, the counter-ion of $Li^+$, namely $X^-$, is a halogenide anion such as $F^-$, $Cl^-$, $Br^-$, the preferred halogenide anion being $Cl^-$.

According to a first embodiment, the above structure (a1), i.e. $Z=CH_2$, is obtained by reacting one mole of $II_A$ (which $Z^1$ is $CH_2$) with at least one mole of $III_A$ (in which $OZ^2$ is OMe).

That first embodiment is illustrated by the following reaction mechanism, wherein $Z^1$ is $CH_2$, $R^1$ is Ph, $R^2$ is Me and $R^3$ is Me:

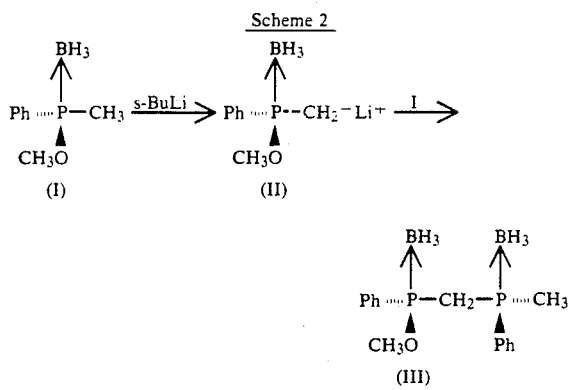

According to a second embodiment, the above structure (a2), i.e. $Z=CH_2CH_2$, is obtained by reacting one mole of $II_A$ (in which $Z^1$ is $CH_2$) with one mole of the very same $II_A$ (in which $Z^1$ is also $CH_2$) in the presence of a mild oxidizing means, preferably $CUX_2$ (in which X is a halogen atom as defined above, and preferably the chlorine atom).

That second embodiment is illustrated by the following reaction mechanism wherein $R^1$ is Ph, $R^2$ is Me, $R^3$ is Me, $Z^1$ is $CH_2$ and Z is $CH_2CH_2$:

Scheme 3

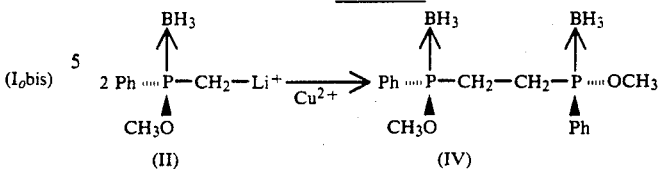

According to a third embodiment, the above structures (b1-B6) are obtained by reacting two moles of $II_A$ (wherein $Z^1$ is $CH_2$) with one mole of a dihalogeno compound of the formula $R^2AX_2$ wherein R, A and X are defined as indicated above.

That third embodiment is illustrated by the following reaction mechanism wherein $R^1$ is Ph, $R^2$ is Me, $R^3$ is Me, $Z^1$ is $CH_2$ and Z is $CH_2$—$SiR_2$—$CH_2$ in the final product:

Scheme 4

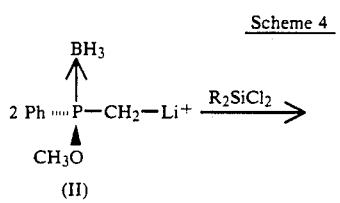

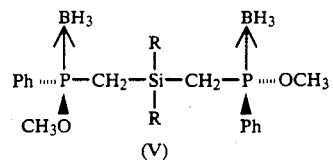

In the above first, second and third embodiments, the reaction is carried at a temperature of from $-100°$ C. to $+30°$ C. In the first embodiment, a temperature gradient of from $-40°$ C. to $+15°$ C. can be used. In the second embodiment, a temperature gradient of from $-40°$ C. to $+20°$ C. can be used. In the third embodiment, a temperature gradient of from $-40°$ C. to $0°$ C. can be used.

The preferred reaction solvent for carrying out of said first, second and third embodiments is anhydrous THF.

The preferred temperature for carrying out of said first, second and third embodiments is $0°$ C.

Moreover from a chiral point of view, it is possible to replace easily in the formula $I_o$ an oxy group $OR^2$ or $R^3$ or both by a group which is more nucleophilic than said oxy groups $OR^2$ and $R^3$. See for such a replacement the methods given in examples 4 and 5 hereinafter.

BEST MODE OF THE INVENTION

According to the best mode of this invention, chiral compounds of the formula $I_o$ (i.e. to be more precise of the formula $I_o$bis) are provided, in which $R^1$ is Ph, Ph substituted by 1-3 alkoxy groups wherein each alkoxy moiety contains from 1 to 4 carbon atoms, 2-naphthyl, $R^2$ is a $C_1$-$C_6$ alkyl group, $R^3$ is a $C_1$-$C_6$ alkoxy group, and Z has the (a1), (a2), (b4), (b5) or (b6) structure.

These chiral compounds are obtained according to reaction schemes 2-4.

Moreover these chiral compounds can be easily transformed into other chiral compounds of the formula $I_o$ by replacing the oxy groups $OR^2$ and $R^3$ into other more nucleophilic radicals, such as for instance aryl groups, alkoxy-substituted aryl groups and alkyl groups.

Further advantages and characteristics of this invention will be understood more clearly from the following description of preparative examples. Taken as a whole this information does not imply a limitation but is given by way of illustration.

EXAMPLE 1

Methyl (R)-[[(R)-methylphenylphosphino]methyl]phenylphosphonite-diborane

Alternate nomenclature: (R,R)-[methylphenylphosphino]-[methoxyphenylphosphino]methane-diborane

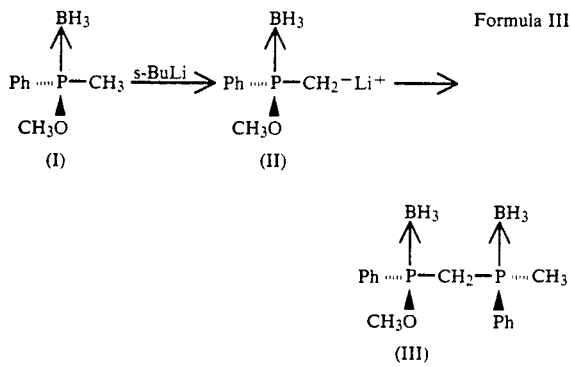

Formula III

In a 50 ml reactor, 2 mmol of phosphinite-borane of the formula I are dissolved in 3 ml of anhydrous THF at $-78°$ C. under an inert atmosphere (nitrogen or argon). Into the solution thus obtained, 2 mmol of s-BuLi are added under stirring. 0.25 h after the addition of s-BuLi the temperature of the reaction medium is brought to $-40°$ C., and the reaction medium is kept at $-40°$ C. for 0.5 h in order to allow the formation of the anions

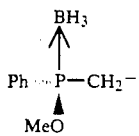

of the formula II. Then 2 mmol of phosphinite-borane of the formula I are added and the temperature of the reaction medium is left to increase slowly up to $+15°$ C. for 2 h. After hydrolysis, solvent evaporation and washing with water, the expected product is extracted with $CH_2Cl_2$ then purified by filtration over silica using toluene as an eluent.

Yield: 70%.

The characteristics of the product then obtained are as follows:

Colorless oil
$[\alpha] = -56°$ (c=1; CHCl$_3$)
RMN$^1$H (CDCl$_3$): major: $\delta = 0.1-1.5$ (6H,q.l.,$^1J_{BH}=80$); 1.83 (3H, d, J=10.2); 2.60 (2H, m); 3.61 (3H, d., J=12.5); 7.25-7.5 (6H,m); 7.5-7.8(4H,m) minor: $\delta = 1.56$ (3H,d.,J=10.38); 3.35 (3H,d., J=11.8)

RMN$^{13}$C (CDCl$_3$): $\delta = 11.39$ (d.,J=39); 30.19 (d.d,J=23,J=32); 54.01 (S); 128.47-132.36 (aromatic). (minor: $\delta = 12.89$ (d.,J=39)).

RMN$^{31}$P (CDCl$_3$): $\delta = +8.38$ (q,$^1J_{PB}=67.5$). +113.10 (q,$^1J_{PB}=69.8$).

IR (pure) $\nu = 3057$; 2945 (C—H); 2385; 2254 (B—H); 1437; 1417; 1173; 1115; 1064; 1034

| Microanalysis for: | $C_{15}H_{24}O_2 2B_2P_2$ | |
|---|---|---|
| Mass: | 304.1332 | 304.1334 |
| | Calculated | found |
| % C | 59.21 | 58.01 |
| % H | 7.89 | 7.72 |

EXAMPLE 2

(S,S)-1,2-bis(methoxyphenylphosphino)ethane-diborane

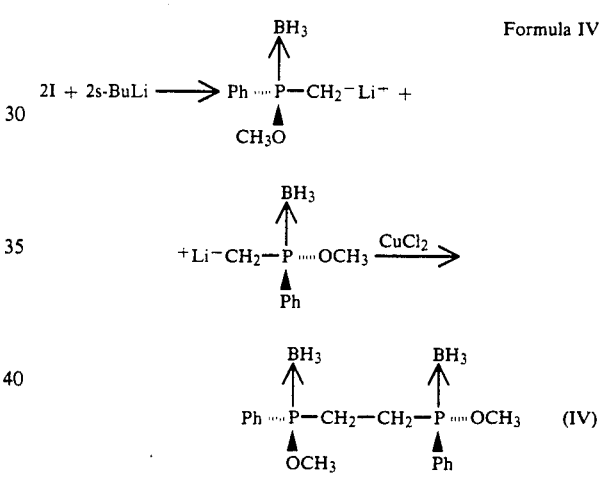

Formula IV

In a 50 ml reactor, 2 mmol of phosphinite-borane of the formula I are dissolved in 3 ml of anhydrous THF at $-78°$ C. under an inert atmosphere. Into the solution thus obtained, 2 mmol of s-BuLi are added under stirring. 0.25 h after the addition of s-BuLi the temperature of the reaction medium is brought to $-40°$ C., and the reaction medium is kept at $-40°$ C. for 0.5 h in order to allow the formation of the anions of the formula II. Then 10 mmol of CuCl$_2$ are added and the reaction medium is left in the air for 12 h. After hydrolysis, solvent evaporation and washing with water, the expected product is extracted with $CH_2Cl_2$ then purified by filtration over silica using toluene as an eluent.

Yield: 88%.
MP=111°-115° C.
RMN $^{31}$P= +118 $J_{PB}$=58 Hz
$[\alpha]_D = -115.1°$ (c=1; CHCl$_3$)
RMN$^1$H=0-1.5 (6H,m); 1.9-2.4 (4H, m); 3.6 (6H,d) 7.4-7.8 (10, m)
IR: $\nu_{BH}$=2370 cm$^{-1}$.

EXAMPLE 3

(R,R)-bis[(methoxyphenylphosphino)methyl]diphenyl-silyl-diborane

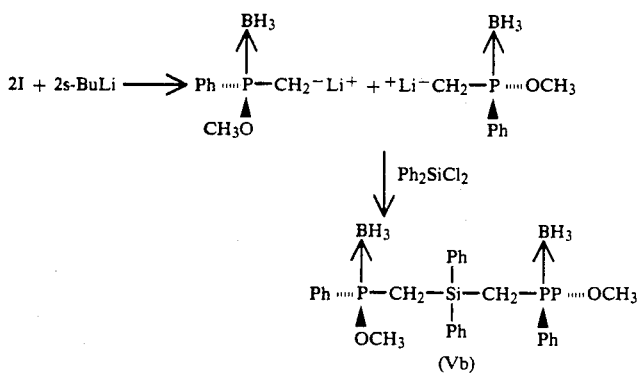

(Vb)

In a 50 ml reactor, 2 mmol of phosphinite-borane of the formula I are dissolved in 3 ml of anhydrous THF at −78° C. under an inert atmosphere. Into the solution thus obtained, 2 mmol of s-BuLi are added under stirring. 0.25 h after the addition of s-BuLi the temperature of the reaction medium is brought to −40° C., and the reaction medium is kept at −40° C. for 0.5 h in order to allow the formation of the anions of the formula II. Then 1 mmol of dichlorodiphenylsilane is added and the temperature of the reaction medium is raised slowly up to 0° C., and kept at 0° C. for 2 h. After hydrolysis, solvent evaporation and washing with water, the expected product is extracted with $CH_2Cl_2$ then purified by filtration over silica using toluene as an eluent.

Yield: 90%.

Thick colorless oil.

RMN$^1$H (CDCl$_3$): δ=0.0-1.5 (6H,q.l.,$^2J_{BH}$=95); 2.13-2.43 (4H,q.d.,J=7.7, J=16.4); 3.28 (6H,d,J=12.28); 7.05-7.85 (20H,m).

(the other diastereoisomer: 3.25 (6H,d,J=12.27))

RMN$^{31}$P (CDCl$_3$): +116.74 (m)

(the other isomer: +114 (m))

EXAMPLE 4

Use of the Diphosphinite-Diborane of Example 2 (Formula IV) in the Preparation of DIPAMP-Diborane

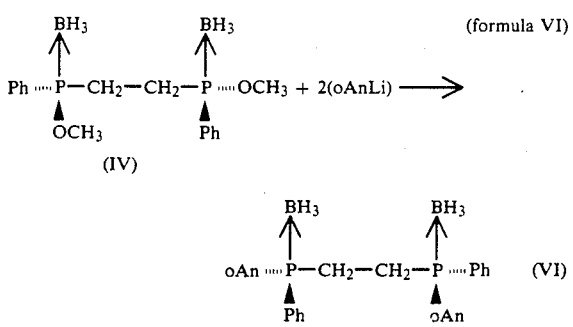

In a 50 ml reactor, 2 mmol of phosphinite-borane of the formula IV (obtained according to the method of example 2) are dissolved in 3 ml of anhydrous THF at −78° C. under an inert atmosphere. In the solution thus obtained, 2,1 mmol of oAnLi are added under stirring. 0.25 h after the addition of oAnLi, the temperature of the reaction medium is raised slowly up to 0° C. over a period of time of 2 h. After hydrolysis, solvent evaporation and washing with water, the expected product is extracted with $CH_2Cl_2$ then purified by filtration over silica using toluene as an eluent.

Formula Vb

Yield: 80%

MP=163° C. (in accordance with the literature).

EXAMPLE 5

Use of the Diphosphinite-Diborane of Example 2 (Formula IV) in the Preparation of Diphosphine-Diborane (Formula VIII)

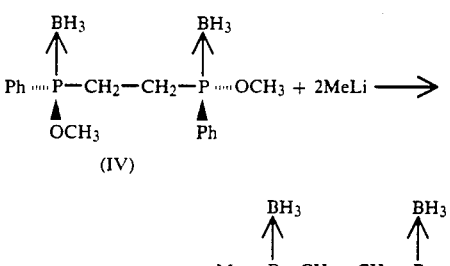

In a 50 ml reactor, 2 mmol of phosphinite-borane of the formula IV (obtained according to the method of example 2) are dissolved in 3 ml of anhydrous THF at −78° C. under an inert atmosphere. In the solution thus obtained, 2,1 mmol of MeLi are added under stirring. 0.25 h after the addition of MeLi, the temperature of the reaction medium is raised slowly up to 0° C. over a period of time of 2 h. After hydrolysis, solvent evaporation and washing with water, the expected product is extracted with $CH_2Cl_2$ then purified by filtration over silica using toluene as an eluent.

Yield: 90%

MP=166°-168° C.

IR: 2378, 1457, 1420, 1065 cm$^{-1}$

RMN$^1$H: 0-2 ppm (6H,m); 1.55 (6H,m); 1.8-2.2 (4H,m); 7.2-7.9 (10H,m)

Analysis for $C_{16}H_{26}B_2P_2$ calculated: C=63.58%; H=8.61%. found: C=63.68%; H=8.55%.

EXAMPLE 6

Obtention of (−)-DIPAMP

The chiral (−)-DIPAMP product is obtained (from the (−)-DIPAMP-diborane compound of example 4 of the formula VI) according to a known technique (see scheme 3 on page 6358 of the above cited S. JUGE et al.

article) disclosed by T. IMAMOTO et al. and involving the use of HNEt$_2$ as a borane-decomplexing means.

According to said known technique of T. INAMOTO et al. a 0.5M solution of (−)-DIPAMP-diborane of the formula VI is heated, in the presence of an excess of HNEt$_2$, at 50° C. for 12 h. Then, the excess of amine is distilled off and the distillation residue is filtered over a short silica column, using toluene as an eluent. The expected diphosphine compound [i.e. (−)-DIPAMP] is recovered from the first eluted fractions. MP=103° C. (in accordance with the literature).

EXAMPLE 7

Obtention of 1,2-bis(methylphenylphosphino)ethane $$\text{Me}\cdots\text{P}-\text{CH}_2-\text{CH}_2-\text{P}\cdots\text{Ph}$$
$$\uparrow \qquad\qquad\qquad \uparrow$$
$$\text{Ph} \qquad\qquad\qquad \text{Me}$$

That chiral product is obtained according to the method of the above example 6 from the compound of example 5 of the formula VIII.

EXAMPLE 8

BNPPMDS-diborane

The chiral BNPPMDS-diborane compound is prepared from the compound of example 3 of the formula Vb, according to the method of example 4, with the difference that oAnLi is replaced by an equivalent amount of 2-naphthyllithium.

EXAMPLE 9

Obtention of BNPPMDS

That chiral compound is obtained according to the method of the above example 6 from the BNPPMDS-diborane compound of example 8.

EXAMPLE 10

(−)-BNPE-diborane

The chiral (−)-BNPE-diborane compound is prepared from the compound of example 2 of the formula IV, according to the method of example 4, with the difference that oAnLi is replaced by an equivalent amount of 2-naphthyllithium.

EXAMPLE 11

Obtention of (−)-BNPE

That chiral compound is obtained according to the method of the above example 6 from the (−)-BNPE-diborane compound of example 10.

What is claimed is:

1. A BH$_3$-containing phosphinite compound is prepared from the compound selected from the group consisting of diphosphinite-borane compounds of the formula $$\begin{array}{c} \text{BH}_3 \quad\ \text{BH}_3 \\ \uparrow \qquad \uparrow \\ \text{R}^1-\text{P}-\text{Z}-\text{P}-\text{R}^1 \\ | \qquad | \\ \text{OR}^2 \quad \text{R}^3 \end{array} \qquad (\text{I}_o)$$

wherein
R$^1$ and R$^2$, identical or different, represent each a C$_1$-C$_{18}$ alkyl, C$_5$-C$_{18}$ cycloalkyl, C$_7$-C$_{18}$ aralkyl or C$_5$-C$_{14}$ aryl group which can bear functional groups,
R$^3$ represents a C$_1$-C$_{18}$ alkyl, C$_5$-C$_{18}$ cycloalkyl, C$_7$-C$_{18}$ aralkyl, C$_6$-C$_{14}$ aryl, C$_1$-C$_{18}$ alkoxy, C$_5$-C$_{18}$ cycloalkyloxy, C$_7$-C$_{18}$ aralkyloxy or C$_5$-C$_{14}$ aryloxy group,
Z represents a bridge linking the two phosphinite P atoms, said bridge being (i) a hydrocarbon chain having from 1 to 12 catenary C atoms or (ii) a heterohydrocarbon chain comprising from 1 to 12 catenary C atoms and at least one catenary heteroatom selected from the group consisting of O, S, Si, P and N.

2. A diphosphinite-borane compound according to claim 1, having the chiral structure $$\begin{array}{c} \text{BH}_3 \quad\ \text{BH}_3 \\ \uparrow \qquad \uparrow \\ \text{R}^1\cdots\text{P}-\text{Z}-\text{P}\cdots\text{R}^3 \\ \uparrow \qquad \uparrow \\ \text{R}^2\text{O} \quad\ \text{R}^1 \end{array} \qquad (\text{I}_o\text{bis})$$

wherein R$^1$, R$^2$, R$^3$ and Z are defined as indicated above.

3. A diphosphinite-borane compound according to claim 1 or 2, wherein R$^1$ and R$^2$ represent each an unsubstituted aryl group or an aryl group substituted by one or several C$_1$-C$_4$ alkoxy, CN, CF$_3$, F, Cl, Br and I.

4. A diphosphinite-borane compound according to claim 1 or 2, wherein said bridge Z has one of the following structures:
 (a) —(CH$_2$)$_n$—, and
 (b) —(CH$_2$)$_m$—A—(CH$_2$)$_p$—
wherein
n, m and p, identical or different, represent each an integer of from 1 to 6,
A represents O, S, PR, SiR$_2$ or NR, in which R is C$_1$-C$_4$ alkyl, C$_5$-C$_6$ cycloalkyl, C$_5$-C$_{10}$ aryl, benzyl or phenethyl.

5. A diphosphinite-borane compound according to claim 1 or 2, wherein said bridge Z is selected from the group consisting of
 (a1) —CH$_2$—,
 (a2) —CH$_2$CH$_2$—,
 (b1) —CH$_2$—O—CH$_2$—,
 (b2) —CH$_2$—S—CH$_2$—,
 (b3) —CH$_2$—P(Ph)—CH$_2$—,
 (b4) —CH$_2$—Si(Me)$_2$—CH$_2$—,
 (b5) —CH$_2$—Si(Ph)$_2$—CH$_2$— or
 (b6) —CH$_2$—Si(Bz)$_2$—CH$_2$—

6. A diphosphinite-borane compound according to claim 1 or 2, wherein R$^3$ is a C$_1$-C$_5$ alkoxy group.

7. A chiral diphosphinite-borane compound of the formula I$_o$bis according to claim 2, wherein R$^1$ is Ph, Ph substituted by 1-3 alkoxy groups wherein each alkoxy moiety contains from 1 to 4 carbon atoms, 2-naphthyl, R$^2$ is a C$_1$-C$_5$ alkyl group, R$^3$ is a C$_1$-C$_5$ alkoxy group, and Z is
 (a1) —CH$_2$—,
 (a2) —CH$_2$CH$_2$—,
 (b4) —CH$_2$—Si(Me)$_2$—CH$_2$—,
 (b5) —CH$_2$—Si(Ph)$_2$—CH$_2$— or
 (b6) —CH$_2$—Si(Bz)$_2$—CH$_2$—

8. A chiral diphosphinite-borane compound of the formula I$_o$bis according to claim 2, which is (R,R)-bis[-(methoxyphenylphosphino)methyl]diphenylsilyl-diborane.

9. A method for preparing a diphosphinite-borane compound of the formula I$_o$ or I$_o$bis according to claim 1 or 2, said method comprising reacting an organometallic compound deriving from a phosphinite-borane compound with a non-metallic phosphinite-borane compound.

* * * * *